United States Patent [19]
McClanahan et al.

[11] Patent Number: 5,602,325
[45] Date of Patent: Feb. 11, 1997

[54] EXHAUST SENSOR HAVING FLAT PLATE CERAMIC SENSING ELEMENT AND A SEALING PACKAGE

[75] Inventors: Mark R. McClanahan, Goodrich; Kaius K. Polikarpus, Davison, both of Mich.

[73] Assignee: General Motors Corporation, Detroit, Mich.

[21] Appl. No.: 547,082

[22] Filed: Oct. 23, 1995

Related U.S. Application Data

[63] Continuation-in-part of Ser. No. 505,026, Jul. 21, 1995, abandoned, which is a continuation-in-part of Ser. No. 313,688, Sep. 27, 1994, abandoned.

[51] Int. Cl.$^6$ ..................................................... G01N 27/04
[52] U.S. Cl. .......................... 73/23.31; 73/31.05; 204/426; 204/424; 338/38
[58] Field of Search .............................. 73/23.31, 23.32, 73/31.05, 31.06; 204/424, 426, 428; 338/34, 221, 229, 230

[56] References Cited

U.S. PATENT DOCUMENTS

| | | | |
|---|---|---|---|
| 4,040,930 | 8/1977 | Dillon | 204/426 |
| 4,225,842 | 9/1980 | Schlesselman et al. | 338/34 |
| 4,403,207 | 9/1983 | Murphy et al. | 338/34 |
| 4,535,316 | 8/1985 | Wertheimer et al. | 73/23.32 |
| 4,656,863 | 4/1987 | Takami et al. | 73/31.05 |
| 4,802,369 | 2/1989 | Morii | 204/424 |
| 4,958,514 | 9/1990 | Takami et al. | 338/34 |
| 5,031,445 | 7/1991 | Kato et al. | 204/424 |
| 5,089,133 | 2/1992 | Kato et al. | 204/424 |
| 5,139,639 | 8/1992 | Holleboom | 204/424 |
| 5,228,975 | 7/1993 | Yamada et al. | 204/424 |
| 5,467,636 | 11/1995 | Thompson et al. | 73/23.31 |

FOREIGN PATENT DOCUMENTS

| | | | |
|---|---|---|---|
| 63750 | 5/1980 | Japan | 204/428 |
| 137056 | 6/1986 | Japan | 73/31.05 |

Primary Examiner—Hezron E. Williams
Assistant Examiner—Daniel S. Larkin
Attorney, Agent, or Firm—Cary W. Brooks

[57] ABSTRACT

The invention includes a flat plate exhaust gas sensor having a plurality of layers of glass and steatite immediately surrounding a flat plate sensing element. A ceramic body surrounds each layer of solid-state, sintered glass and steatite and extends from each layer to a protective metal housing. A ceramic plunger presses the layers of glass and steatite. The plunger surrounds electrical connectors to the sensing element to prevent damage to the connector from heat.

7 Claims, 3 Drawing Sheets

EXHAUST SENSOR HAVING FLAT PLATE CERAMIC SENSING ELEMENT AND A SEALING PACKAGE

FIELD OF THE INVENTION

This application is a continuation-in-part of U.S. Ser. No. 08/505,026 filed Jul. 21, 1995, now abandoned, which, itself, is a continuation-in-part of U.S. Ser. No. 08/313,688 filed Sep. 27, 1994, now abandoned.

This invention relates to combustion engine exhaust sensors, and more particularly to a sensor having a flat plate sensing element and sealing package including a tubular ceramic body surrounding multilayer seals.

BACKGROUND OF THE INVENTION

FIG. 1 illustrates a flat plate automotive exhaust sensor of the prior art. The exhaust sensor includes a heated flat plate sensing element 138 which is carried in a tubular housing 116 and held in position by a first cement composition 140, glass seal 142 and a second cement composition 144, each of which extends from the flat plate heating element to the tubular wall 116 of the sensor. The heated flat plate sensing element includes an air reference channel formed therein and is positioned within the sensor to provide communication with an air source in the upper portion of the sensor. A glass seal prevents exhaust gas from traveling from the lower end of the sensor through the tubular housing and into the upper portion of the sensor, which would contaminate the air in the air reference channel of the electrolyte body. Glass seals are desirable because they are easily formed by firing glass frit in a furnace. Such sensors are used to monitor constituents in an automotive combustion engine exhaust gas stream such as oxygen, and to adjust the operation of the engine including the air fuel ratio.

However, the glass seal, heated flat plate sensing element and the tubular shell have different thermal coefficients of expansion. When the sensor is exposed to high temperatures associated with combustion engine exhaust, the glass seal, heated flat plate sensing element and tubular shell expand and contract at different rates. This often results in leakage paths between the glass seal and the tubular shell, the flat plate sensor element being damaged by expansion of the glass seal, or the flat plate exhaust sensor coming loose within the housing.

The present invention overcomes many of the deficiencies of the prior art sensors.

SUMMARY OF THE INVENTION

The invention includes a flat plate exhaust gas sensor having a plurality of layers of glass and steatite immediately surrounding a flat plate sensing element. A ceramic body surrounds each layer of glass and steatite and extends from each layer to a protective metal housing. A ceramic plunger presses the layers of glass and steatite while hot in an assembly operation. The plunger surrounds electrical connectors to the sensing element to prevent damage to the connector from heat and to electrically insulate each lead. The plunger also serves as a continuous sealing surface to prevent water intrusion into the air reference channel of the sensing element.

These and other objects, features and advantages will become apparent from the following brief description of the drawings, detailed description and appended claims and drawings.

DETAILED DESCRIPTION

Figure 1:
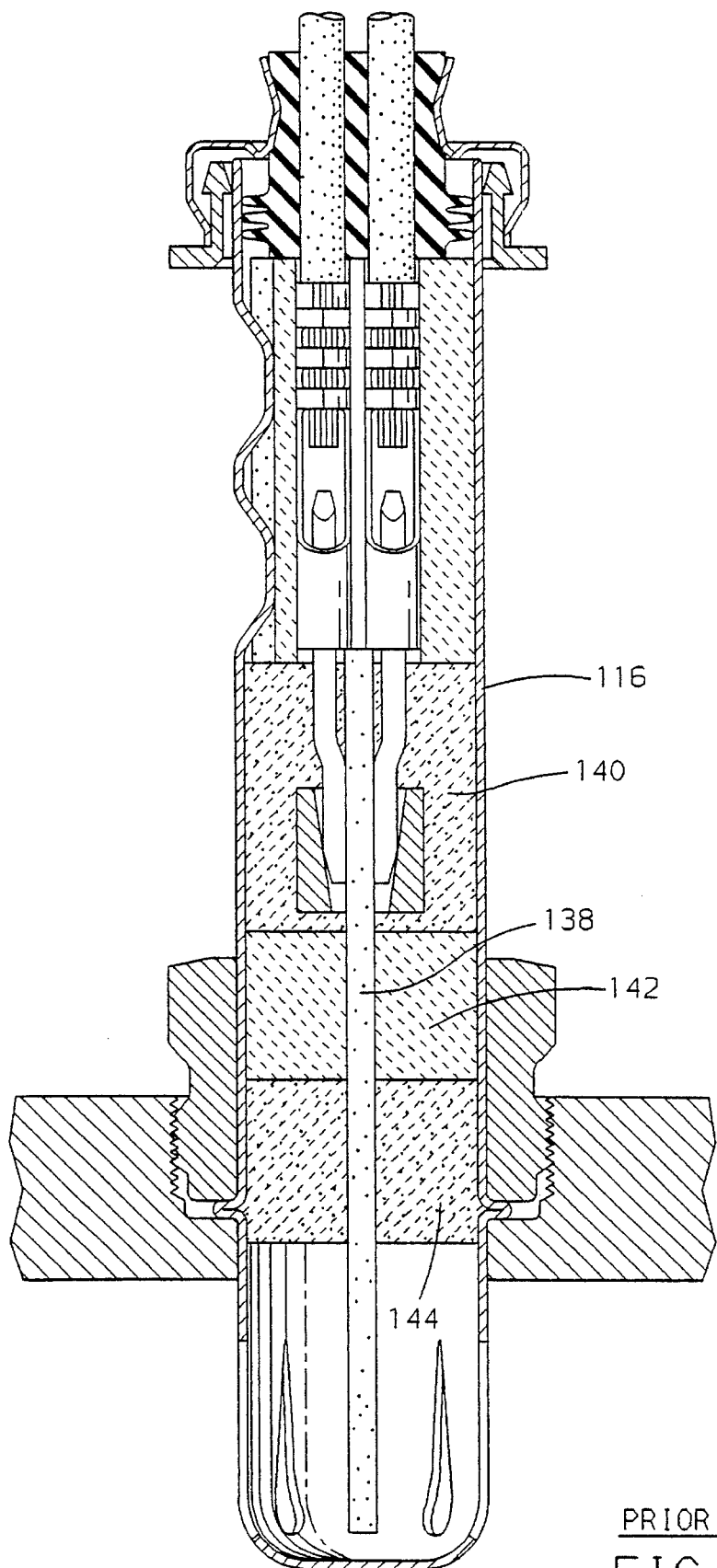
FIG. 1 illustrates a prior art sensor with a glass seal.
Figure 2:
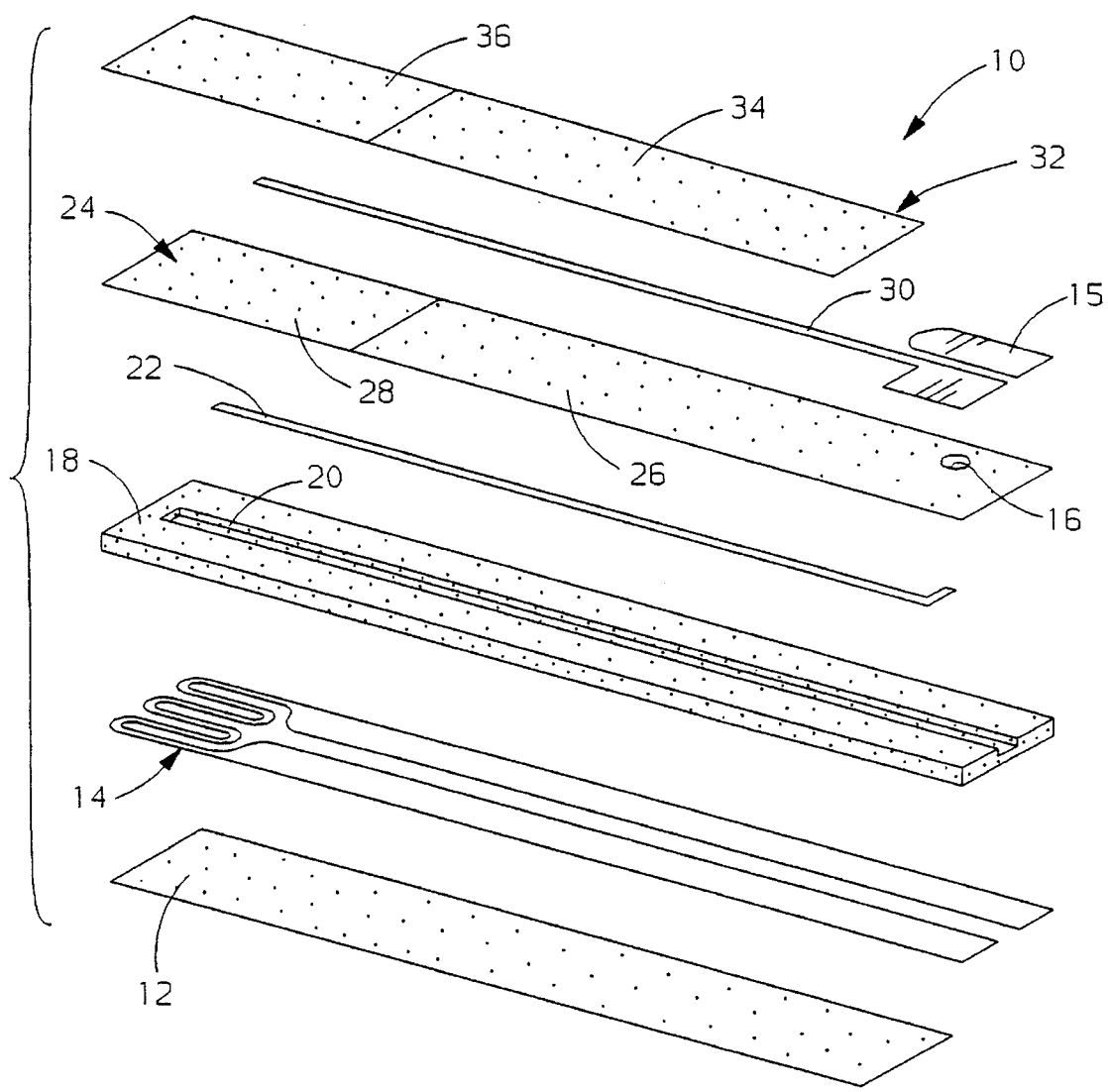
FIG. 2 is an exploded view of a heated flat plate exhaust gas constituent sensing element useful in the present invention.

FIG. 2 illustrates an exhaust sensor 10 according to the present invention including, in overlapping relationship, the following elements: a heater dielectric protective tape 12; a printed heater 14; an alumina substrate 18 including an air reference channel 20 formed therein; an inner electrode 22 printed on one side of a co-cast composite tape 24 including a dielectric portion 26 and an electrolyte body portion 28; an outer electrode 30 and sensor pads printed on the other side of the co-cast composite tape 24; and a protective outer tape 32 including a dense alumina portion 34 and a porous alumina portion 36 overlying the electrolyte body portion 28 of the composite tape 24. The tape 24 has a hole 16 formed therein to provide contact between pad 15 and inner electrode 22. The co-cast composite tape 24 includes a first portion 26 which is a dielectric material such as alumina and the second portion 28 is a dense electrolyte material such as zirconia near one end of the sensing element 10. The co-cast composite tape 24 may be made from a variety of methods such as slurry casting, roll compaction or calendaring. Such processes are disclosed in U.S. patent application Ser. No. 08/196863 filed Feb. 15, 1994, now U.S. Pat. No. 5,384,030, assigned to the assignee of the present invention, the disclosure of which is hereby incorporated by reference. The various layers of the sensing element are fired together to form a single flat plate sensing 10 element.

The invention includes an exhaust sensor having a heated flat plate sensing element 10 as illustrated in FIG. 2 and described above or a conventional flat plate sensing element.

Figure 3:
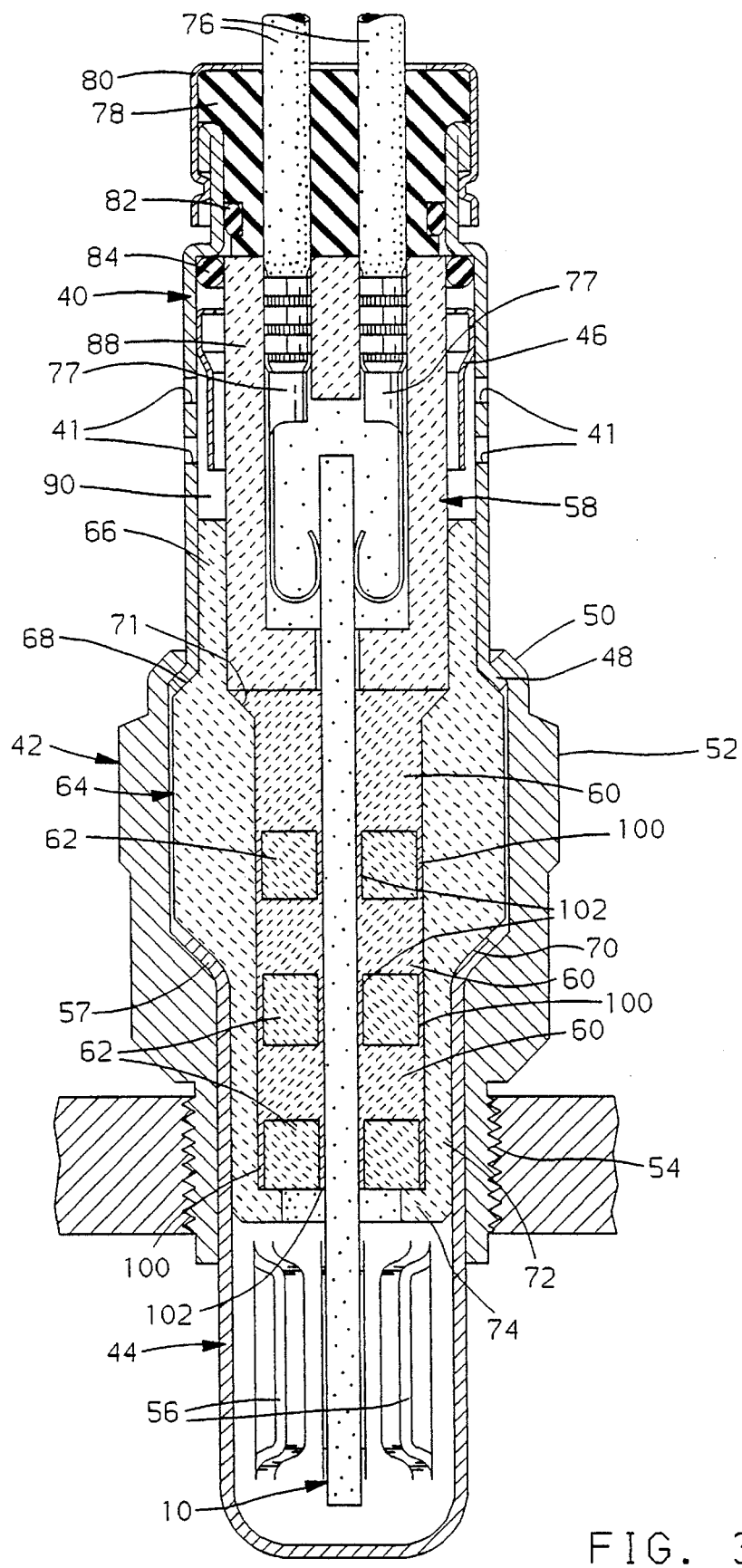
FIG. 3 illustrates an exhaust gas sensor including a sealing package according to the present invention.

FIG. 3 illustrates an exhaust gas sensor according to the present invention and including a unique sealing package. The exhaust sensor includes an upper tubular shell 40, a middle shell 42 and a bottom tubular shell 44. The upper tubular shell may include vents 41 formed therein for removing heat from the sensor element. A stainless steel retainer 46 may be press fit to the inside wall of the upper tubular shell 40 and functions to form the lower gland wall of the above O-ring seal 84 and also serves as a water splash shield to prevent water from coming through the vents 41 in the upper shell. The upper tubular shell 40 includes an outwardly flared foot 48 at a lower end which is situated beneath a crimped portion 50 near the top of the middle shell 42. The middle shell 42 includes wrench flats 52 formed on an outer surface and a threaded portion 54 for threading into a manifold boss of an exhaust system (pipe or manifold). The lower tubular shell 44 includes louvers 56 or perforations formed therein through which exhaust gas enters and contacts the sensing element 10. The lower tubular shell rests on a chamfer 57 on the inside wall of the middle shell 42. The upper tubular shell 40, middle shell 42 and lower tubular shell 44 make up a sensor housing.

Within the sensor housing, a flat plate exhaust gas constituent sensing element 10 is carried. An upper ceramic plunger 58, preferably steatite, is positioned in the upper shell 40 of the housing and has a hole formed therein for receiving an upper portion of the sensing element 10. A middle portion of the sensing element 10 is surrounding by a plurality of alternating layers of glass 60 and a spacer 62, preferably steatite. The glass layer 60 is made from a solid glass frit preform which preferably comprises borosilicate. Each glass layer has a thickness ranging from about 0.05 inches to about 0.20 inches. Each steatite layer also has a thickness ranging from about 0.05 inches to about 0.20 inches. The width or diameter of the glass 60 and steatite layers 62 will vary with the inner diameter of the ceramic tube; the larger the tube, the larger the glass and spacer diameter. The plurality of alternating layers of glass 60 and steatite 62 are surrounded by a tubular-shaped ceramic body 64 such as a ceramic oxide, nitride or carbide material. The tubular-shaped ceramic body 64, steatite spacers 62 and sensing element 10 are assembled with sufficient tolerances, about 0.001 to about 0.01 inches, so that upon heating of the glass layer 60 and plunging as described hereafter, a thin layer of glass 100 flows down between an end of the spacer 62 and the ceramic body 64, and a thin layer of glass 102 flows down between the inside edge of the spacer 62 and the sensing element 10. The tubular-shaped ceramic body 64 is preferably at least one oxide selected from the group consisting of alumina, zirconia, or steatite. The tubular-shaped ceramic body 64 includes an upper portion 66 having substantially straight walls, a thicker middle portion and a relatively thinner lower portion 72. The tubular-shaped ceramic body 64 also includes upper, lower and inside sloped shoulders 68, 70, 71 respectively. The thinner lower portion 72 also includes an inwardly extending lip 74 which supports the plurality of layers of solid-state, sintered glass 60 and steatite 62. The term "solid-state, sintered glass" as used herein refers to glass sintered via a high temperature process often referred to as "liquid phase sintering" or "viscous phase sintering" wherein the glass becomes liquid as it densifies, and solidifies as it cools. An upper ceramic plunger 58 is received in the upper portion 66 of the tubular-shaped ceramic body 64 and contacts the upper first layer of glass 60. The steatite plunger 58 is held in position by the inside sloped shoulder 71 formed on the inside wall of the tubular-shaped ceramic body 64 where the sloped shoulder connects the upper thin portion 66 and the thicker middle portion of the ceramic body 64.

Wires 76 extend through a fluropolymer stopper 78 and communicate with the flat plate sensing element 10 by way of electrical connectors 77 attached to the wires. The fluropolymer stopper 78 is carried in a metal cap 80 connected to the top of the upper metal tube 40.

The sensor may include a plurality of O-rings 82, 84 for frictionally fitting the components within the housing and providing an environmental seal. The upper steatite plunger 58 includes a wall 88 extending from the ceramic body 64 to an O-ring 84 near the top of the upper tubular shell 40. A gap 90 is provided between the inside wall of the upper tubular shell 40 and an outside wall of the steatite plunger 58. Holes 41 formed in the upper tubular shell 40 communicate with the gap 90. Thus, should a seal fail at the shell sloped shoulder 70, exhaust gas flow travel up along the outer surface of the ceramic tube 64, past the crimp 50, and out the perforations or holes 41 formed in the upper tubular shell 40 and will not contaminate the air reference for the sensing element 10. The O-ring 84 also prevents water intrusion which might contaminate the air reference of the element 10 (i.e., provides an environmental seal).

The tubular-shaped ceramic body 64, multiple alternating layers of glass 60 and steatite 62 surrounding the flat plate sensing element 10 and the steatite ceramic plunger 58 are placed in a furnace and heated to a temperature at which the glass becomes workable about 850°–950° C. A load of about 1 to about 10 lbs. is applied to the steatite ceramic plunger 58 to compress the glass layers 60 while in the molten state to fill the clearance gaps between the sensing element 10 and spacer 62, and between the spacer 62 and ceramic body 64. Alternatively, a weight of 0.25 to about 2.5 lbs. may be set on top of the plunger 58 for glass compression through the heating process. The ceramic assembly is allowed to cool. When the assembly is cooled to room temperature, the tubular shell 44 is dropped into the middle shell 42 and the upper tubular shell 40 is fit over the ceramic assembly, which is then crimped into the middle metallic shell 42.

The flat plate sensing element 10 includes an alumina support substrate 18 and a zirconia dense electrolyte portion 24 for measuring the presence of various constituents within the exhaust gas stream. The ceramic tube is preferably made from a ceramic oxide such as alumina to have substantial strength and to substantially match the coefficient of expansion of the flat plate sensing element 10. The glass sealing layers 60 are utilized because they provide a good seal preventing exhaust gas from moving up through the sensor housing and entering the air reference channel 20 of the sensing element 10. The various layers of steatite 62 are utilized because they have a coefficient of expansion similar to the alumina body of the sensing element 10 and they provide good thermal resistance to heat flow through the sensor package which would prevent excessive heating of the fluropolymer stopper 78.

The glass layer 60 preferably includes borosilicate and about 7 weight percent mullite for fracture toughness and equal distribution of the glass on hot pressing. Preferably the glass has a coefficient of thermal expansion of about 4.8 in/in° C. from room temperature to 250° C.; a glass transition temperature of about 468° C., and a softening point of about 696° C. The steatite layer 62 has a coefficient of thermal expansion of about 8.5 to 9.3 in/in° C. at 40°–900° C. The coefficient of thermal expansion of the alumina ceramic body 64 and the heated sensing element 10 having an alumina support substrate are both about 8.3 in/in° C. at 40°–1000° C.

The use of a plurality of alternating glass 60 and steatite layers 62 within a ceramic tube provides for a more compatible ceramic-to-ceramic seal formed between the ceramic tube 64 and the plurality of layers, and with respect to the plurality of layers and the sensing element 10.

The embodiments of the invention in which an exclusive property or privilege is claimed are defined as follows:

1. An exhaust gas sensor comprising:

an outer housing;

a flat plate sensing element carried within the housing;

a plurality of alternating layers of solid-state, sintered glass and spacer surrounding a portion of said flat plate sensing element; and a ceramic body surrounding each of said layers of solid-state, sintered glass and spacer, said ceramic body extending from said layers to the outer housing, further comprising a thin layer of solid-state, sintered glass between the ceramic body and each spacer, and a thin layer of solid-state, sintered glass between each spacer and the flat plate sensing element.

2. An exhaust sensor as set forth in claim 1 wherein said ceramic body has a cylindrical portion extending upward from said layers of solid-state, sintered glass and spacer; and further comprising a ceramic plunger having a hole formed therein for receiving an upper portion of the flat plate sensing element, said ceramic plunger having a lower portion received within the upwardly extending cylindrical portion of the ceramic body, said plunger having an upper portion secured in the housing by an O-ring, and middle portion spaced a distance from the housing to provide a gap therebetween; said housing having holes formed in a portion thereof immediately adjacent said gap.

3. An exhaust sensor as set forth in claim 1 wherein said flat plate sensing element comprises an alumina substrate, and said ceramic body comprises alumina.

4. An exhaust sensor as set forth in claim 1 wherein said outer housing comprises an upper shell welded to a middle shell welded to a lower shell and said ceramic body conforms to an inside wall of the middle shell.

5. An exhaust sensor as set forth in claim 2 further comprising wires having electrical connectors communicating with the flat plate sensing element, and wherein said ceramic plunger surrounds said electrical connectors to prevent heat damage.

6. An exhaust sensor as set forth in claim 1 wherein said ceramic body comprises an inwardly extending lip at a lower end of the ceramic body for supporting the plurality of layers of solid-state, sintered glass and spacer.

7. An exhaust sensor as set forth in claim 1 wherein each spacer comprises steatite.

* * * * *